United States Patent
Black et al.

(10) Patent No.: US 6,981,314 B2
(45) Date of Patent: Jan. 3, 2006

(54) METHOD OF FORMING A LEAD

(75) Inventors: Damon Ray Black, Dallas, TX (US); Terry Daglow, Allen, TX (US); John Erickson, Plano, TX (US); Robert Earl Jones, Wylie, TX (US); B. Reno Lauro, Murphy, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 526 days.

(21) Appl. No.: 10/042,992

(22) Filed: Jan. 9, 2002

(65) Prior Publication Data

US 2002/0055765 A1    May 9, 2002

Related U.S. Application Data

(62) Division of application No. 09/760,437, filed on Jan. 12, 2001, now abandoned, which is a division of application No. 09/299,702, filed on Apr. 26, 1999, now Pat. No. 6,216,045.

(51) Int. Cl.
*H01R 43/00* (2006.01)

(52) U.S. Cl. .................. 29/825; 600/373; 600/377; 600/381; 607/116; 607/122

(58) Field of Classification Search .............. 29/825; 607/116, 119, 122; 600/373–375, 381, 377
See application file for complete search history.

(56) References Cited

U.S. PATENT DOCUMENTS

| | | |
|---|---|---|
| 3,333,045 A | 7/1967 | Fisher et al. |
| 3,367,339 A | 2/1968 | Sessions |
| 3,416,534 A | 12/1968 | Quinn |
| 3,596,662 A | 8/1971 | Bolduc |
| 3,825,015 A | 7/1974 | Berkovits |
| 4,161,952 A | 7/1979 | Kinney et al. |
| 4,285,347 A | 8/1981 | Hess |
| 4,369,791 A | 1/1983 | Friedman |
| 4,374,527 A | 2/1983 | Iversen |
| 4,379,462 A | 4/1983 | Borkan et al. |
| 4,432,377 A | 2/1984 | Dickhudt |
| 4,437,474 A | 3/1984 | Peers-Trevarton |
| 4,458,695 A | 7/1984 | Peers-Trevarton |
| 4,469,104 A | 9/1984 | Peers-Trevarton |
| 4,485,268 A | 11/1984 | Kaplan |
| 4,498,482 A | 2/1985 | Williams |
| 4,514,589 A | 4/1985 | Aldinger et al. |
| 4,549,556 A | 10/1985 | Tarjan et al. |
| 4,559,951 A | 12/1985 | Dahl et al. |
| 4,572,605 A | 2/1986 | Hess |
| 4,592,372 A | 6/1986 | Beranek |
| 4,608,986 A | 9/1986 | Beranek et al. |
| 4,651,751 A | 3/1987 | Swendson et al. |

(Continued)

FOREIGN PATENT DOCUMENTS

EP    0 293 499 A1    12/1988

(Continued)

*Primary Examiner*—Richard Chang
(74) *Attorney, Agent, or Firm*—Peter R. Lando

(57) ABSTRACT

An implantable, substantially isodiametric, low resistance implantable lead having at least one electrode positioned in a stimulation/sensing portion of the lead as well as a method of manufacturing the same. At least the stimulation/sensing portion is unitized through partially surrounding and supporting insulation and conductive element(s) of the stimulation/sensing portion with a fused matrix of material having mechanical properties consistent with a body of the lead.

4 Claims, 3 Drawing Sheets

U.S. PATENT DOCUMENTS

| | | |
|---|---|---|
| 4,699,157 A | 10/1987 | Shonk |
| 4,934,049 A | 6/1990 | Kiekhafer et al. |
| 4,947,866 A | 8/1990 | Lessar et al. |
| 5,121,754 A | 6/1992 | Mullett |
| 5,304,219 A | 4/1994 | Chernoff et al. |
| 5,330,521 A | 7/1994 | Cohen |
| 5,374,285 A | 12/1994 | Vaiani et al. |
| 5,409,461 A | 4/1995 | Steinman |
| 5,417,208 A | 5/1995 | Winkler |
| 5,458,629 A | 10/1995 | Baudino et al. |
| 5,466,253 A | 11/1995 | Doan |
| 5,483,022 A | 1/1996 | Mar |
| 5,524,338 A * | 6/1996 | Martyniuk et al. ............ 29/825 |
| 5,555,618 A * | 9/1996 | Winkler ........................ 29/825 |
| 5,562,722 A | 10/1996 | Racz et al. |
| 5,733,322 A | 3/1998 | Starkebaum |
| 5,796,044 A | 8/1998 | Cobian et al. |
| 5,827,272 A | 10/1998 | Breining et al. |
| 5,851,222 A | 12/1998 | Taylor et al. |
| 5,897,584 A | 4/1999 | Herman |
| 6,185,463 B1 | 2/2001 | Baudino |
| 6,236,892 B1 | 5/2001 | Feler |
| 6,253,111 B1 | 6/2001 | Carner |

FOREIGN PATENT DOCUMENTS

| | | |
|---|---|---|
| EP | 0 329 112 A1 | 8/1989 |
| EP | 0 622 089 A2 | 11/1994 |
| WO | WO95/22371 | 8/1995 |
| WO | WO98/34678 | 8/1998 |
| WO | WO/9847560 | 10/1998 |

* cited by examiner

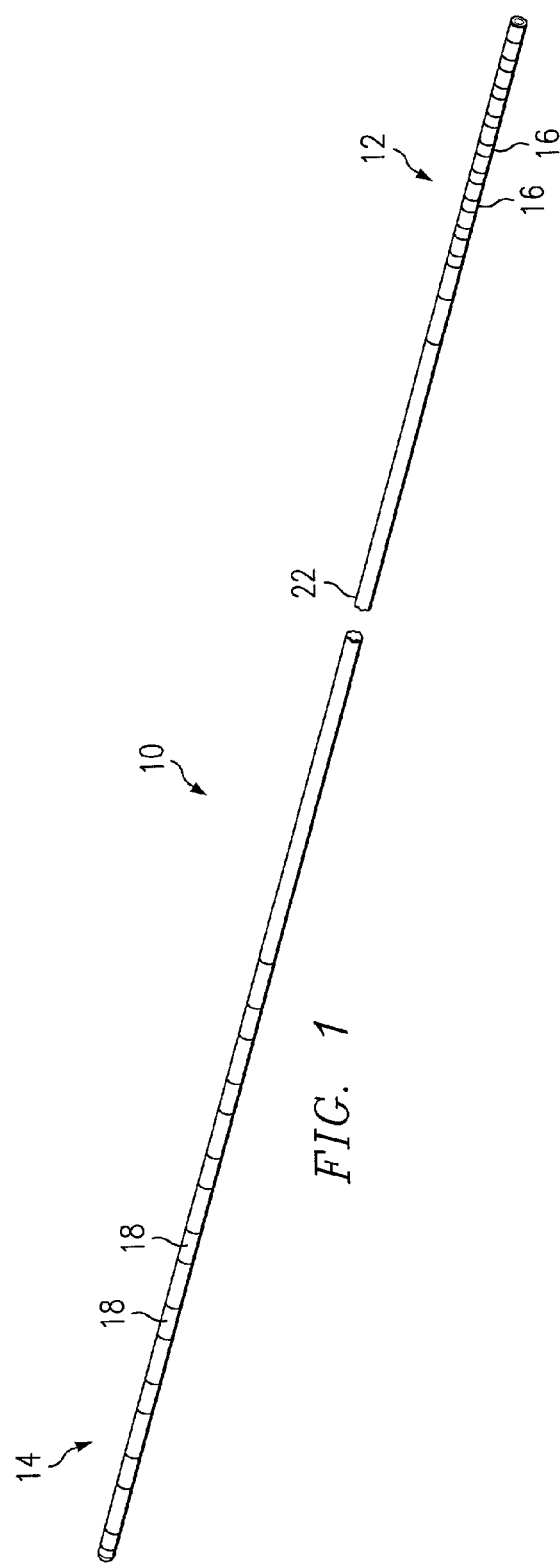
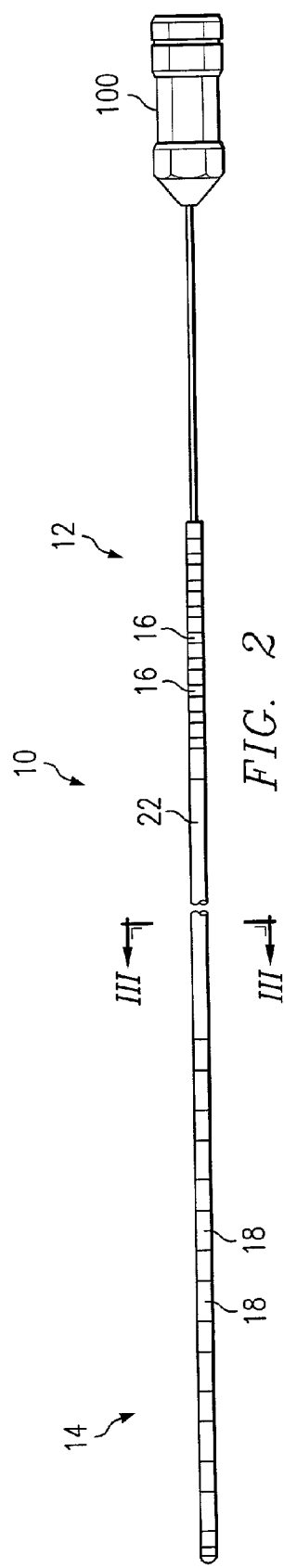

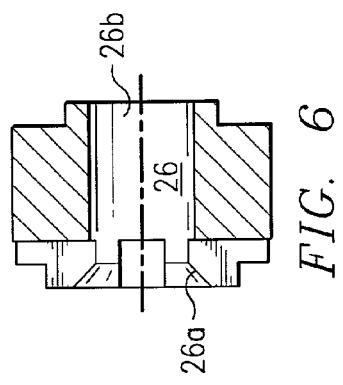
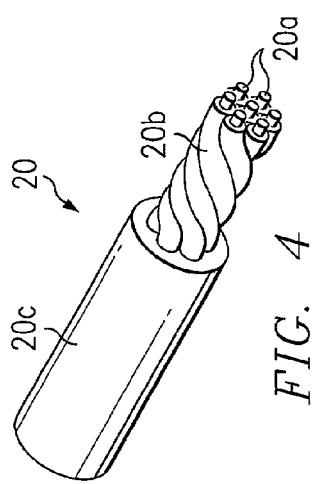
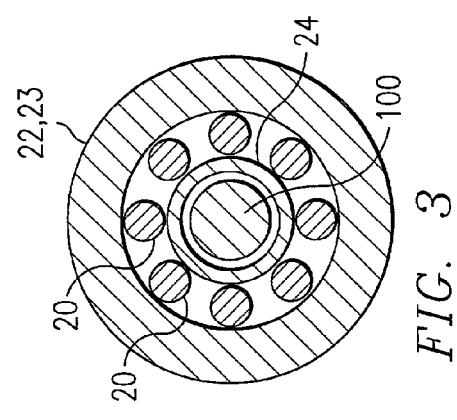
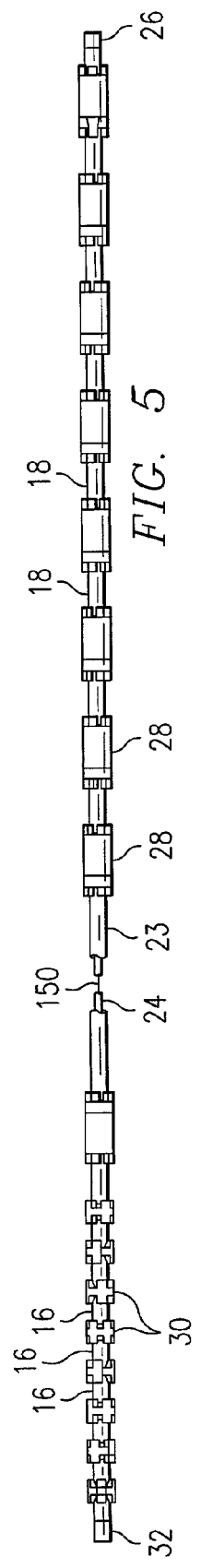

METHOD OF FORMING A LEAD

RELATED APPLICATIONS

This is a division of U.S. patent application Ser. No. 09/760,437, filed Jan. 12, 2001, now abandoned, which is a division of U.S. patent application Ser. No. 09/299,702, filed Apr. 26, 1999, issued as U.S. Pat. No. 6,216,045.

FIELD OF THE INVENTION

The present invention relates to a lead, and in particular, to an implantable lead and a method of manufacturing such lead.

BACKGROUND OF THE INVENTION

Implantable leads having ring electrodes can be used in a variety of applications, including delivery of electrical stimulation to surrounding tissue, neural or otherwise, as well as measuring electrical energy produced by such tissue. Whether serving in a stimulation capacity or a sensing capacity, such leads are commonly implanted along peripheral nerves, within the epidural or the intrathecal spaces of the spinal column, about the heart, and in the brain.

Notwithstanding the application, the common requirements for such implantable leads include flexibility, strength, and durability. The extent of such qualities, of course, is dependent upon the nature of the use, for example, temporary or permanent implantation. While material selection and certain construction techniques can be tailored to assist in meeting these prescribed characteristics, an overriding consideration in the design of such leads is achieving at least an isodiametric stimulation/pacing portion thereof.

The benefits of achieving desired levels of flexibility, strength, and durability are intuitive. The isodiametric characteristic is likely less obvious. Depending upon the application, an isodiametric lead can reduce the potential for damage to the lead during insertion (for example, when a lead is passed through an insertion needle to reach a patient epidural space) and/or placement, improve the ability of the lead to pass through tissue or a vascular system, and is more resistant to being immobilized by tissue growth at a permanent implantation site.

Differing techniques have been used to produce isodiametric leads. One such technique concerns adhering a plurality of elements (i.e., conductive electrodes, conductive terminals, and spacing insulative tubing material) to produce a generally integral body. Tubing material separates a stimulation/sensing portion (i.e., alternating insulative tubing material and electrodes) from a terminal portion (i.e., alternating insulative tubing material and terminals). The electrodes, terminals, and tubing are independently formed but are intended to be isodiametric. Understandably, dimension variances in any one element can result in a lead having a varying diameter.

Of further interest, to strengthen the plurality of element interfaces found in the stimulation/sensing portions and terminal portions of these leads, a composition, for example, medical grade epoxy, is injected within an interior of the leads in and about the stimulation/sensing portions and the terminal portions. While this technique does typically effect stabilization and strengthening of these critical regions, the end result can also be that these regions are too rigid and even brittle.

Other techniques include applying a ring electrode(s) about an exterior surface of insulative tubing that forms the main body of the lead. The insulative tubing may be prepared to receive the electrode, for example, milled to remove an amount of material substantially equal to the material thickness of the ring electrode. Alternatively, the insulative tubing may be unprepared, for example, a ring electrode is simply "crimped" to a diameter substantially equal to the otherwise unadulterated diameter of the tubing.

For all of the methods described above, a finished lead is still comprised of a plurality of independent components brought together in an effort to form an isodiametric cross-section. Element misalignment, inaccuracies in grinding, variances in electrode material thickness or individual element dimensions, or over/under-crimping could respectively result in at least undesirable variances in lead diameter.

Accordingly, a need exists for a lead, as well as a method of fabricating such lead, that provides a requisite level of flexibility, strength, and durability, while further providing a true isodiametric body for at least the stimulation/sensing portion of the lead.

SUMMARY OF THE INVENTION

One aspect of the present invention is directed to an implantable lead including a lead body, having a distal end and a proximal end, whereas the lead body is formed of a material having prescribed mechanical properties. Extending from the distal end of the lead body, a first region includes a plurality of electrodes. A first insulative material, having mechanical properties consistent with the material of the lead body, separates adjacent electrodes. Extending from the proximal end of the lead body, a second region includes at least one terminal. A second insulative material, having mechanical properties consistent with the material of the lead body, separates adjacent terminals. A conductor couples each terminal to at least one corresponding electrode of the plurality of electrodes, wherein the conductor(s) extends along an interior passage defined by the lead body, first region, and second region. In addition to the at least one conductor, the interior passage of the first region is substantially filled with a third insulative material having mechanical properties consistent with the material of the lead body.

Another aspect of the present invention concerns a method of forming a substantially isodiametric lead. Specifically, such lead has a prescribed diameter and includes at least one electrode separated from at least one terminal by a lead body, wherein the at least one electrode is electrically coupled to the at least one terminal by a conductor passing through a passage defined by at least the lead body. The forming steps include assembling the at least one electrode and the at least one terminal relative to the lead body to form an assembly, including connecting the at least one electrode to the at least one terminal via the conductor. The assembly is subjected to an over-molding process that over molds the assembly with a first material to form an intermediate assembly. This first material is compatible with and has mechanical properties consistent with a material of the lead body. Ultimately, the intermediate assembly is processed to remove all material of the intermediate assembly in excess of the prescribed diameter.

An object of the present invention is to avoid the shortcomings of known leads and manufacturing techniques for the same.

Another object of the present invention is to provide a method of forming a lead having a true isodiametric body for at least the stimulation/sensing portion of the lead.

Another object of the present invention is to provide a lead having a true isodiametric body for at least the stimulation/sensing portion of the lead.

Another object of the present invention is to provide a lead having a low resistance from a terminal to a coupled electrode to reduce energy consumption during system operation.

Other aspects, objects, and advantages of the present invention will be apparent to those of ordinary skill in the art having reference to the following Specification together with the provided drawings.

BRIEF DESCRIPTION OF THE DRAWINGS

In reference to the following figures, like reference numerals and letters indicate corresponding elements:

FIG. 1 is a perspective view of a multi-electrode lead in accordance with the present invention;

FIG. 2 is a plan view of another embodiment of a multi-electrode lead in accordance with the present invention;

FIG. 3 is a sectional view of the lead of FIG. 2, taken along line III—III;

FIG. 4 is a perspective view of a preferred conductor;

FIG. 5 is a plan view of an assembly of elements on a mandrel used to form a lead in accordance with the present invention;

FIG. 6 is a sectional view of a transitional element;

DETAILED DESCRIPTION OF THE PREFERRED EMBODIMENTS

Figure 7:
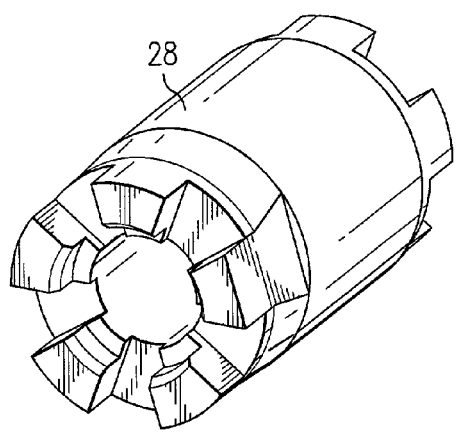
FIG. 7 is a perspective view of an electrode spacer.

Various embodiments, including preferred embodiments, will now be described in detail below with reference to the drawings:

FIG. 1 illustrates a preferred embodiment of multi-electrode lead 10. While the leads illustrated and generally discussed here have eight electrodes, lead 10 of the present invention may be constructed having any number of electrodes (i.e., one or more):

Lead 10 includes a proximal end 12 and a distal end 14. The proximal end 12 includes a plurality of electrically conductive terminals 16, and the distal' end 14 includes a plurality of electrically conductive electrodes 18. While typically each terminal 16 is electrically connected to a single electrode 18 via a conductor 20 (FIG. 3), a terminal 16 can be connected to two or more electrodes 18.

Terminals 16 and electrodes 18 are preferably formed of a non-corrosive, highly conductive material. Examples of such material include stainless steel, MP35N, platinum, and platinum alloys. In a preferred embodiment, terminals 16 and electrodes 18 are formed of a platinum-iridium alloy.

Spanning between electrodes 18 of the distal end 14 and terminals 16 of the proximal end 12, body 22 is formed from a medical grade, substantially inert material, for example, polyurethane, silicone, or the like. While the specific material used for body 22 is not critical to the present invention, body 22 must be non-reactive to the environment of the human body, provide a flexible and durable (i.e., fatigue resistant) exterior structure for the components of lead 10, and insulate adjacent terminals 16 and/or electrodes 18.

Serving as a sheath, body 22 substantially provides the exterior structure that contains the internalized elements of lead 10. Specifically, body 22 provides an enclosure for each conductor 20 that connects a terminal 16 with one or more electrodes 18. Each conductor 20 is formed of a conductive material that exhibits the desired mechanical properties of low resistance, corrosion resistance, flexibility, and strength. For consideration, however, it should be appreciated that in the context of a multiple electrode lead 10, a plurality of conductors 20 are required to fit within the interior of body 22. Accordingly, the cross-sectional area of each conductor 20 is restricted. As but one example, for a lead in accordance with the present invention that has an outer diameter of approximately 0.055 inches, conductor 20 could be on the order of approximately 0.0065 inches.

While stranded bundles of stainless steel, MP35N, platinum, platinum-iridium alloy, drawn-brazed silver (DBS) or the like can be used, the preferred embodiment of conductors 20 utilizes wires formed of multi-strands of drawn-filled tubes (DFT), as illustrated in FIG. 4. Each strand is formed of a low resistance material 20a and is encased in a high strength material 20b (preferably, metal). A selected number of strands (seven, for this example) are wound and coated with an insulative material 20c. With regard to the operating environment of the present invention, insulative material 20c protects the individual conductors 20 if body 22 were breached during use. Wire formed of multi-strands of drawn-filled tubes to form conductors 20, as discussed here, is available from Temp-Flex Cable, Inc. (City, State).

In addition to providing the requisite strength, flexibility, and resistance to fatigue, conductors 20 formed of multi-strands of drawn-filled tubes, in accordance with the preferred embodiment, provide a low resistance alternative to other conventional materials. Specifically, a stranded wire, or even coiled wire, of approximately 60 cm and formed of MP35N or stainless steel or the like would have a measured resistance in excess of 30 ohms. In contrast, for the same length, a wire formed of multi-strands of drawn-filled tubes, as illustrated in FIG. 4, could have a resistance less than 4 ohms. Accordingly, in a preferred embodiment, each conductor 20, having a length equal to or less than 60 cm, has a resistance of less than 25 ohms. In a more preferred embodiment, each conductor 20, having a length equal to or less than 60 cm, has a resistance equal to or less than 10 ohms. In a most preferred embodiment, each conductor 20, having a length equal to or less than 60 cm, has a resistance of less than 4 ohms.

As an alternative embodiment, body 22 can further encompass stylet tubing 24 (FIG. 3). Stylet tubing 24 extends from the proximal end 12 to a point within a distal portion of lead 10; however, in a preferred embodiment, stylet tubing 24 extends to cap electrode 34. In cooperative reference to FIG. 2, stylet tubing 24 operatively receives stylet 100 for purposes of allowing better control over lead 10 during placement.

Lead Assembly

While the following discussion provides but one example of a sequence of steps to form a lead similar to that illustrated in FIGS. 2 and 3. One having ordinary skill in this art shall appreciate that the following steps may be performed in a differing order or otherwise inconsequentially modified to still yield the present invention. Consequently, such minor variations are still regarded as being within the scope of the present invention and should be construed in such manner.

Furthermore, for purposes of illustration, the following example includes certain physical dimensions to illustrate the relationship between elements as well as effects of differing processes. Accordingly, the provided physical dimensions are used merely for example and shall not restrict the scope of the present invention.

The following illustrative example concerns the construction of an eight electrode, epidural lead that accommodates a stylet. One skilled in the art shall appreciate, however, that a lead in accordance with the present invention may have more than or less than eight electrodes and/or have a larger or smaller diameter than the following example and remain within the scope of this disclosure.

In reference to FIG. 5, stylet tubing 24 is positioned over mandrel 150. Stylet tubing 24 has an outer diameter of approximately 0.02 inches.

Depending on the quantity of conductors 20 required (e.g., for this illustration, eight) and the size (i.e., diameter) of such conductors 20, arranging and securing conductors 20 can be problematic when they are being arranged and secured about an element having the dimensions of stylet tubing 24.

Figure 11:
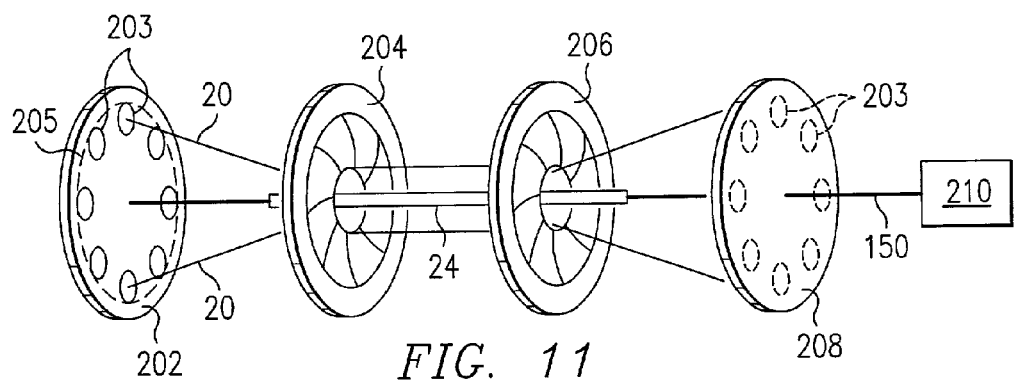
FIG. 11 is a schematic representation of one embodiment of an assembly fixture used to assemble a lead in accordance with the present invention.

While any number of techniques may be used to achieve such arrangement of conductors 20 relative to stylet tubing 24, FIG. 11 illustrates an example of a fixture 200 that can assist in this task. Specifically, fixture 200 includes first rotary clamp 202, iris 204, iris 206, second rotary clamp 208, and clamp 210. Rotary clamps 202 and 208 each include a corresponding plurality of conductor clamps 203. While not required, it is preferred that the plurality of conductor clamps 203 of each rotary claim 202 and 208 be positioned within an arbitrary perimeter 205, whereas perimeter 205 should be equal to or greater than a fully-opened inner diameter of either iris 204 or 206:

As illustrated, mandrel 150, including stylet tubing 24, passes through irises 204 and 206 and second rotary clamp 208 and is secured between clamps 202 and 210. Each conductor 20 similarly passes through irises 204 and 206 and is secured between respective clamps 203 of rotary clamps 202 and 208.

Conductors 20 secured within fixture 200 are prepared for assembly in that a prescribed amount of insulative material 20c is removed at or about the proximal and distal ends of each conductor 20 to expose conductive material 20a and 20b. As will be discussed later, this exposed conductive material 20a and 20b of the proximal and distal ends of each conductor 20 is eventually joined to an electrode 18 and a terminal 16. Accordingly, the exposed conductive material 20a and 20b is arranged at differing positions relative to stylet tubing 24 to accommodate the serial arrangement of terminals 16 and electrodes 18.

The rotational nature of rotary clamps 202 and 208 provides unobstructed access to the in-process lead 10. Specifically, upon securing a single conductor 20 between opposing (or non-opposing) clamps 203, the rotary clamps 202 and 210 are simply rotated to allow access to unoccupied clamps 203.

When all of the conductors 20 are strung between claims 202 and 208, irises 204 and 206 are actuated to close and draw conductor(s) 20 closely about the outer diameter of stylet tubing 24. When conductor(s) 20 are resting against the outer diameter of stylet tubing 24, conductor(s) 20 are secured in place. Conductor(s) 20 may be secured using adhesive and/or subjected to a force applied through use of a temporary or permanent restraint, for example, one or more crimped collars.

While the illustration of FIG. 11 shows but one embodiment of fixture 200, one skilled in the art should appreciate that other techniques/structures may be employed to position conductors 20 adjacent an exterior surface of stylet tubing 24. Specifically, clamps 203 of each rotary clamp 202 and 208 could be moveable along respective radial paths (not shown) that would allow strung conductors 20 to be moved from a first position to a second position adjacent the exterior surface of stylet tubing 24. Alternatively, conductors 20 could initially be secured to one end of stylet tubing 24 and only a single iris could be used to draw the unsecured portions of conductors 20 toward stylet tubing 24. As yet another alternative, while the various alternatives offered provide some mechanism to control the rate of movement and relative positioning of conductors 20, an operator could simply manipulate the conductor(s) 20 to manually position and secure them relative to stylet tubing 24.

Once all conductors 20 are secured to stylet tubing 24, transitional element 26, electrode(s) 18, electrode spacer(s) 28, outer tubing 23, terminal spacer(s) 30, terminal(s) 16, and stylet guide 32 are positioned over, and concentrically arranged with, stylet tubing 24. The arrangement of these elements is in accordance with that illustrated in FIG. 5.

Figure 10:
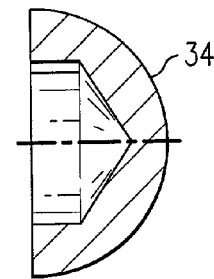
FIG. 10 is a sectional view of a cap electrode.

Transitional element 26 is illustrated in FIG. 6. As will be discussed later, transitional element 26 provides a platform to receive cap electrode 34 (FIG. 10). Transitional element 26 further provides a durable guide 26a to direct a distal end (not shown) of stylet 100 to cap electrode 34 via passage 26b. Transitional element 26 is preferably formed of a conductive material, for example, the same material used to form electrodes 18.

Figure 8:
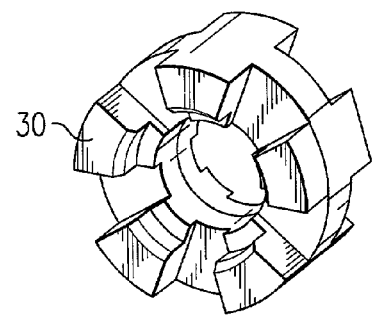
FIG. 8 is a perspective view of a terminal spacer.

Electrode spacer 28 is illustrated in FIG. 7. Similarly, terminal spacer 30 is illustrated in FIG. 8. Functionally, electrode spacer 28 and terminal spacer 30 accurately defines a space between adjacent electrodes 18 and terminals 16, respectively. Electrode spacer 28 and terminal spacer 30 are preferably formed of the same material as outer tubing 23. However, spacers 28 and 30 may be formed of a material that differs from that of outer tubing 23; provided however, any differing material used for electrode spacer 28 and/or terminal spacer 30 must be compatible with and possess largely the same mechanical properties (e.g., non-reactive to the environment of the human body, flexible and durable) as outer tubing 23. At least for purposes of this example, spacers 28, and 30 are formed of a polyurethane material, for example, Bionate 75D (Polymer Tech. Group, City, State). As is noted in FIG. 5, spacers 28 and 30 should have an outer diameter greater than lead 10.

Outer tubing 23 separates electrodes 18 from terminals 16. In a preferred embodiment, outer tubing 23 has a diameter substantially equal to a diameter of lead 10. Alternatively, outer tubing 23 may have a diameter less than lead 10, or a diameter greater than lead 10. In regard to the latter alternative, outer tubing 23 must have a wall thickness greater than a differential between a radius of lead 10 and a radius (to the outer diameter) of outer tubing 23. For this particular example, outer tubing 23 has a nominal outer diameter of approximate 0.055 inches.

Figure 9:
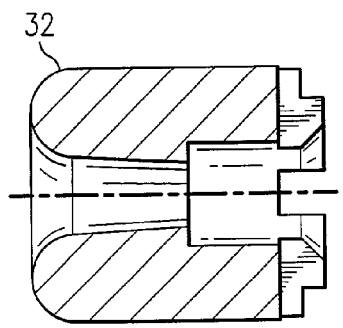
FIG. 9 is a sectional view of a stylet guide.

Stylet guide 32 is illustrated in FIG. 9. Stylet guide 32 provides an inlet to stylet tubing 24. Stylet guide 32 is preferably formed of conductive material, for example, the same material used to form electrodes 18. Stylet guide 32, as well as terminals 16, electrodes 18, and transitional element 26, preferably each have an outer diameter equal to or greater than a nominal diameter of lead 10. In a more preferred embodiment, these elements each have an outer diameter greater than a nominal diameter of lead 10.

Following the assembly of each of the elements described above, terminals 16 and electrodes 18 are joined to their respective conductors 20. Generally, each terminal 16 (and each electrode 18) is positioned relative to exposed conductive material 20a and 20b of a conductor 20 and is joined in a manner that facilitates a transfer of electrical energy, for example, resistance weld or laser weld. Once all terminals 16 and electrodes 18 are secured, stylet guide 32 is secured to a proximal-most terminal 16, and transitional element 26 is secured to a distal-most electrode 18. Provided transitional element 26 and stylet guide 32 are formed a conductive material, these elements may be secured using a process consistent with that used to join terminals 16 and electrodes 18 with conductors 20. Otherwise, transitional element 26 and stylet guide 32 can be joined using an adhesive, cement or the like.

The completed assembly (FIG. 5) is then over-molded, using well known injection molding techniques, using a material having mechanical properties consistent with a material(s) used to form outer tubing 23, electrode spacer 28, and terminal spacer 30. In a preferred embodiment, the over-molding material and the material of outer tubing 23, electrode spacer 28, and terminal 28 are the same.

This process has the beneficial effect of unitizing the element assembly to form lead 10. Moreover, electrode spacers 28 and terminal spacers 30 are placed in a state of flow, which, at least in part, results in a filling of regions between terminals 16/electrodes 18 and stylet guide 24. Consequently, terminals 16 and electrodes 18 are partially surrounded (i.e., along an interior surface) and supported by a fused matrix of; material. Importantly, as electrode spacers 28 and terminal spacers 30 are formed of a material mechanically equivalent to that of body 22/outer tubing 23, the stimulation/sensing portion and terminal portion of lead 10 are stabilized and strengthened while also retaining their flexible properties.

The over-molded assembly (not shown) is then subjected to a grinding process to remove all excess material. In a preferred process, the over-molded assembly is subject to centerless grinding, wherein excessive material, including over-molded material, electrode material, terminal material, and the like, is removed. Pursuant to the described over-molding and grinding of the entire lead assembly, an isodiametric lead is obtained, which is further free of any gaps or voids between insulative material and conductive material that may otherwise exist in conventional devices.

Following the grinding process, cap electrode 34 is affixed to transitional element 26 using conventional means, for example, resistance welding, laser welding, or the like.

While addressed in part above, as the invention has been described herein relative to a number of particularized embodiments, it is understood that modifications of, and alternatives to, these embodiments, such modifications and alternatives realizing the advantages and benefits of this invention, will be apparent to those of ordinary skill in the art having reference to this specification and its drawings. It is contemplated that such modifications and alternatives are within the scope of this invention as subsequently claimed herein, and it is intended that the scope of this invention claimed herein be limited only by the broadest interpretation of the appended claims to which the inventors are legally entitled.

What is claimed is:

1. A method for forming a substantially isodiametric lead having a prescribed diameter and at least one electrode separated from at least one terminal by a lead body, wherein the at least one electrode is electrically coupled to the at least one terminal by a conductor passing through a passage defined by the lead body, comprising the steps of:

assembling the at least one electrode and the at least one terminal relative to the lead body to form an assembly, including connecting the at least one electrode to the at least one terminal via the conductor;

over-molding the assembly with a first material to form an intermediate assembly, wherein the first material is compatible with and has mechanical properties consistent with a second material of the lead body; and removing at least a portion of the first material of the intermediate assembly in excess of the prescribed diameter of the lead, where the lead comprises the at least one electrode, the at least one terminal and the lead body.

2. A method in accordance with claim 1, wherein the at least one electrode has an outer diameter greater than the prescribed diameter prior to the removing step.

3. A method in accordance with claim 1, wherein the at least one terminal has an outer diameter greater than the prescribed diameter prior to the removing step.

4. A method in accordance with claim 1, wherein the removing step involves subjecting the intermediate assembly to at least a centerless grinding process.

* * * * *

UNITED STATES PATENT AND TRADEMARK OFFICE
CERTIFICATE OF CORRECTION

PATENT NO. : 6,981,314 B2  
DATED : January 3, 2006  
INVENTOR(S) : Damon Ray Black et al.

It is certified that error appears in the above-identified patent and that said Letters Patent is hereby corrected as shown below:

<u>Column 3,</u>  
Line 48, after "more)", delete ":" and insert -- . --.

<u>Column 5,</u>  
Line 31, delete "claim" and insert -- clamp --.  
Line 59, delete "claims" and insert -- clamps --.

Signed and Sealed this

Second Day of May, 2006

JON W. DUDAS  
*Director of the United States Patent and Trademark Office*